United States Patent
Chen et al.

(10) Patent No.: US 9,784,883 B2
(45) Date of Patent: Oct. 10, 2017

(54) MULTI-SPECTRAL STATIC CT APPARATUSES

(71) Applicants: Tsinghua University, Beijing (CN); Nuctech Company Limited, Beijing (CN)

(72) Inventors: Zhiqiang Chen, Beijing (CN); Li Zhang, Beijing (CN); Qingping Huang, Beijing (CN); Yunda Sun, Beijing (CN); Xin Jin, Beijing (CN); Tao Yang, Beijing (CN); Le Shen, Beijing (CN); Ji Zhao, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 259 days.

(21) Appl. No.: 14/577,069

(22) Filed: Dec. 19, 2014

(65) Prior Publication Data
US 2015/0185357 A1 Jul. 2, 2015

(30) Foreign Application Priority Data

Dec. 27, 2013 (CN) .......................... 2013 1 0740971

(51) Int. Cl.
*G01N 23/00* (2006.01)
*G01V 5/00* (2006.01)
(Continued)

(52) U.S. Cl.
CPC ......... *G01V 5/0041* (2013.01); *G01N 23/046* (2013.01); *G01T 1/2985* (2013.01); *G01V 5/005* (2013.01)

(58) Field of Classification Search
CPC ................ G01N 23/046; G01N 23/04; G01N 2223/419; G01N 2223/639; G01N 23/087;
(Continued)

(56) References Cited

U.S. PATENT DOCUMENTS 6,018,562 A * 1/2000 Willson ............... G01N 23/087
378/57
7,813,478 B2 * 10/2010 Nisius ................... G01N 23/04
378/115
(Continued)

FOREIGN PATENT DOCUMENTS

CN 101470082 A 7/2009
CN 102697518 A 10/2012
(Continued)

OTHER PUBLICATIONS

European Search Report dated Oct. 26, 2015 in corresponding European Patent Application No. 14 19 9145.
(Continued)

*Primary Examiner* — Irakli Kiknadze
(74) *Attorney, Agent, or Firm* — Pillsbury Winthrop Shaw Pittman LLP

(57) ABSTRACT

Multi-spectral static CT apparatuses are disclosed. The apparatus includes a ray source in a form of multiple distributed spots, multiple columns of detectors, a data acquisition device, an article carrying and control device, and a multi-spectral projection data processing device. An object of the present disclosure is to combine static CT scanning technology with multi-spectral analysis technology. It has an advantage of a static CT system, such as high scanning speed, simple mechanic structure, and/or cost reduction due to omission of slip ring. It also can perform identification of material in an article, and can be widely
(Continued)

applied in occasions such as safety inspection, and smuggling suppression at customs.

19 Claims, 5 Drawing Sheets

(51) Int. Cl.
*G01T 1/29* (2006.01)
*G01N 23/04* (2006.01)
(58) Field of Classification Search
CPC ............ G01N 2223/643; G01N 23/10; G01N 2223/637; G01N 2223/423; G01N 23/20083; G01N 23/203; G01N 2223/206; G01N 2001/024; G01N 2223/401; G01N 23/06; G01T 1/2985; G01V 5/0041; G01V 5/005; A61B 6/032; A61B 6/4007; A61B 6/508; A61B 6/025; A61B 6/4028; A61B 6/4021; A61B 6/4085; A61B 6/4405; A61B 6/482; A61B 6/06; A61B 6/4241; A61B 6/484; A61B 6/488; A61B 6/5205; A61B 6/541; A61B 6/4014; A61B 6/405; A61B 6/027; A61B 6/4078; A61B 6/4233; A61B 6/505; A61B 6/583; A61B 6/4042; A61B 6/4275; A61B 6/502
USPC ............................................. 378/4, 5, 19, 57
See application file for complete search history.

(56) References Cited

U.S. PATENT DOCUMENTS

| | | | |
|---|---|---|---|
| 7,991,112 B2 | 8/2011 | Chen et al. | |
| 9,159,462 B2* | 10/2015 | Rossl | ..................... A61B 6/032 |
| 2007/0121783 A1 | 5/2007 | Ellenbogen et al. | |
| 2011/0280367 A1* | 11/2011 | Baeumer | ................ A61B 6/032 378/9 |
| 2014/0211917 A1 | 7/2014 | Chen et al. | |
| 2015/0185355 A1 | 7/2015 | Zhang et al. | |

FOREIGN PATENT DOCUMENTS

| | | |
|---|---|---|
| CN | 203149136 U | 8/2013 |
| CN | 103 308 535 | 9/2013 |
| CN | 203178216 U | 9/2013 |
| CN | 203909313 U | 10/2014 |
| EP | 2 889 649 | 7/2015 |
| WO | 2010/138607 | 12/2010 |

OTHER PUBLICATIONS

First Office Action as issued in Chinese Patent Application No. 201310740971.5, dated Nov. 4, 2016.
Second Office Action as issued in Chinese Patent Application No, 201310740971.5, dated Jun. 26, 2017.
Communication pursuant to Article 94(3) EPC as issued in European Patent Application No. 14199145.5, dated May 30, 2017.

* cited by examiner

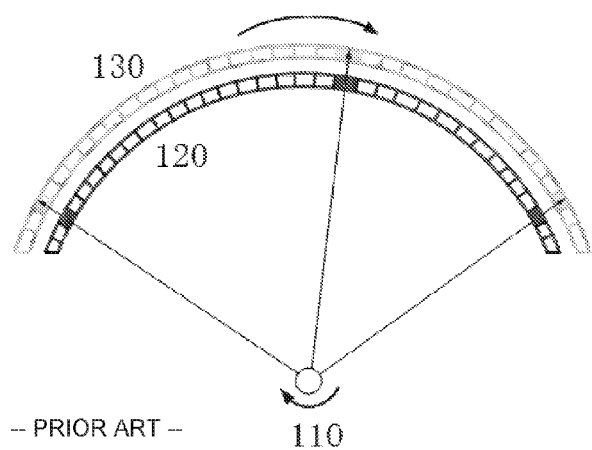
-- PRIOR ART --
Fig. 1
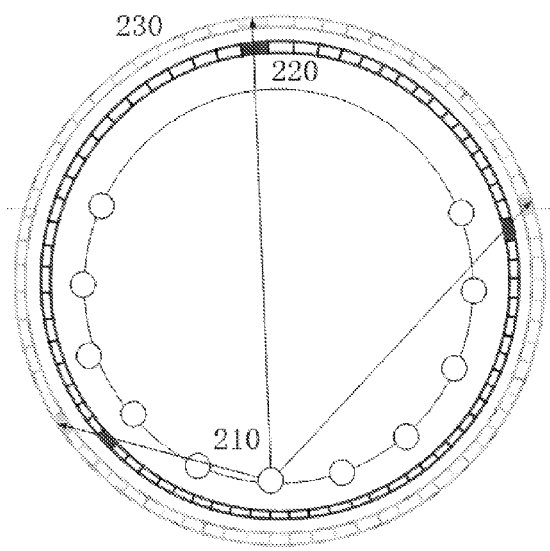
-- PRIOR ART --    Fig. 2

MULTI-SPECTRAL STATIC CT APPARATUSES

This application claims priority to Chinese patent application no. 201310740971.5, filed Dec. 27, 2013, which is incorporated herein in its entirety by reference.

TECHNICAL FIELD

Embodiments of the present disclosure relate to radiation imaging and detection technology, and more particularly, to multi-spectral static Computerized Tomography (CT) apparatuses.

BACKGROUND

CT technology has been playing an important role in occasions such as safety inspection, thanks to its capability of eliminating influence from object overlapping. Conventional CT apparatuses use a slip ring device, and acquire projection data at different angles by rotating X-ray source and detectors. Then, the CT apparatuses reconstruct a tomogram image to obtain information of the inside of the inspected luggage or article. Multi-spectral analysis refers to identifying a material by using a difference in the material's absorption ability with respect to X-rays of different energy spectra. With a combination of the CT technology and the multi-spectral analysis, an existing inspection apparatus can reconstruct atomic number and electron density at any position within the inspected article, and identify a material contained in the article, achieving good effects in detecting substances like explosives or drugs.

SUMMARY

Due to the utilization of slip-ring rotation in data the acquisition process, existing CT apparatuses may have limited scanning speed, huge volume, strict requirements for machining precision, and high cost, which restrict popularity of the CT apparatuses in practical applications. In recent years, the technology of a carbon-nanotube X-ray tube has been introduced to practical application. Unlike a conventional X-ray source, the carbon-nanotube X-ray tube does not require a high temperature to generate rays. Instead, it generates cathode rays based on the principle of discharging of a carbon-nanotube tip, and uses the cathode rays to bombard a target to generate X-rays. Such a X-ray source has an advantage of rapid switch-on/off, and a smaller volume. A "static CT" apparatus without rotation can be formed by arranging the X-ray source in a circle and irradiating X-rays onto the object from different angles. This significantly accelerates the radiography process while omitting the slip-ring structure and saving cost, thereby contributing a lot to the field of safety inspection.

Currently, there has not been any apparent research or report on combined use of static CT and multi-spectral analysis technologies in any radiography system. The existing static CT systems are single-spectrum systems that can reconstruct only a linear attenuation coefficient inside the inspected object. This imposes a significant limitation on the identification ability of such CT systems. In the case of using multi-spectral technology, there are some difficulties in implementing the multi-spectral static CT system. On the one hand, in order to perform multi-spectral analysis, the existing CT apparatus commonly includes a single-spectrum X-ray source and detectors for detecting X-rays of different energy spectra. The detectors are positioned in front and rear columns, such that rays first arrive at the detectors for detecting low energy X-rays, and then arrive at the detectors for detecting high energy X-rays after a spectrum shaping process. FIG. 1 shows a CT apparatus with a slip ring that performs multi-spectral analysis by using a single-spectrum X-ray source 110 and dual-energy detectors 120 and 130 positioned in front and rear columns. The source and the detectors are rotatable with the slip ring, and the detectors do not require coverage of a large range of angles. Each of the low energy detectors 120 penetrated by a ray corresponds to one of the high energy detectors 130 that is also penetrated by the same ray, and thus it facilitates an accurate multi-spectral analysis. A static CT apparatus, which removes the slip-ring structure, uses a distributed ray source 210, and the detectors 220 and 230 cover a large range of angles, and are arranged in a circle, as shown in FIG. 2. In this case, arranging the detectors 220 and 230 in front and rear columns would incur a problem due to the oblique incidence of rays. The obliqueness of rays varies with different angles at which the rays are emitted. Such obliqueness makes it difficult in registering low and high energy data, aggravates cross-talk among adjacent detectors, and leads to degraded resolution in reconstructed images.

On the other hand, there are CT apparatuses that use a different method for performing multi-spectral analysis. They use a multi-spectral X-ray source and a single-energy detector. During the rotation process with the slip ring, the X-ray source is switched between multiple energy spectra at high speed to scan at different energy spectra. This method, however, has intrinsic drawbacks. Since the slip ring rotates at a high speed while the X-ray source is switched between multiple energy spectra, there is a deviation in projection angle between high and low energy data. This deviation is generally negligible when the X-ray source is switched at a high frequency. If this method is applied in a static CT apparatus, it is necessary to set adjacent X-ray sources in multi-spot sources at different energy levels. The number of the X-ray sources should not be very large in consideration of factors like cost and process. Therefore, the deviation in projection angle between high and low energy data cannot be neglected, which will affect accuracy of multi-spectral analysis.

In view of one or more problems with conventional technology, embodiments of the present disclosure provide a multi-spectral static CT apparatus.

According to an aspect of the present disclosure, there is provided a multi-spectral static CT apparatus comprising: a conveyor mechanism that carries and moves linearly an object under inspection; a distributed ray source comprising a plurality of ray source spots that are provided in a plane generally perpendicular to a direction of the object's movement, wherein the plurality of ray source spots at least partially surround the object, and emit X-rays toward the object; a detection device comprising a first column of detectors and a second column of detectors adjacent to the first column of detectors in the direction of the object's movement, wherein the first column of detectors comprises a plurality of detection units having a first energy response, provided in a first plane generally parallel to a plane of the distributed ray source and configured to receive X-rays penetrating the object, and wherein the second column of detectors comprises a plurality of detection units having a second energy response, provided in a second plane generally parallel to the plane of the distributed ray source and configured to receive X-rays penetrating the object; an acquisition device coupled to the detection device and configured to convert the X-rays detected by the first column of detectors into a first digital signal and the X-rays detected by the second column of detectors into a second digital signal; and a processing device coupled to the acquisition device and configured to reconstruct a CT image of the object based on the first and second digital signals.

In some embodiments, the first and/or second columns of detectors have filters.

In some embodiments, each of the ray source spots comprises a carbon-nanotube X-ray tube.

In some embodiments, the first energy response is a response substantially to a low energy component in the X-rays, and the second energy response is a response substantially to a high energy component in the X-rays; and the processing device reconstructs high-energy and low-energy attenuation coefficient images of the object based on the first and second digital signals.

In some embodiments, the processing device reconstructs values of atomic number and/or electron density of the object based on the first and second digital signals.

In some embodiments, the detection device further comprises a third column of detectors adjacent to the second column of detectors in the direction of the object's movement, wherein the third column of detectors comprises a plurality of detection units having a third energy response, provided in a third plane generally parallel to the plane of the distributed ray source and configured to receive X-rays penetrating the object; the acquisition device converts the X-rays detected by the third column of detectors into a third digital signal; and the processing device reconstructs a CT image of the object based on the first, second and third digital signals.

According to another aspect of the present disclosure, there is provided a multi-spectral static CT apparatus comprising: a conveyor mechanism that carries and moves linearly an object under inspection; a first scanning stage comprising: a first distributed ray source comprising a plurality of ray source spots that are provided in a plane generally perpendicular to a direction of the object's movement, wherein the plurality of ray source spots at least partially surround the object, and emit X-rays toward the object, and a first column of detectors comprising a plurality of detection units having a first energy response, wherein the plurality of detection units are provided in a first plane generally parallel to a plane of the first distributed ray source, and configured to receive X-rays penetrating the object; a second scanning stage provided in series with the first scanning stage in the direction of the object's movement, comprising: a second distributed ray source comprising a plurality of ray source spots that are provided in a plane generally perpendicular to a direction of the object's movement, wherein the plurality of ray source spots at least partially surround the object, and emit X-rays toward the object, and a second column of detectors comprising a plurality of detection units having a second energy response, wherein the plurality of detection units are provided in a second plane generally parallel to the plane of the second distributed ray source and configured to receive X-rays penetrating the object; an acquisition device coupled to the first and second columns of detectors, and configured to convert the X-rays detected by the first column of detectors into a first digital signal and the X-rays detected by the second column of detectors into a second digital signal; and a processing device coupled to the acquisition device and configured to reconstruct a CT image of the object based on the first and second digital signals.

In some embodiments, the first distributed ray source generates rays having a spectrum different from that of rays generated by the second distributed ray source.

According to a further aspect of the present disclosure, a multi-spectral static CT apparatus is provided comprising: a conveyor mechanism that carries and moves linearly an object under inspection; a first scanning stage comprising: a first distributed ray source comprising a plurality of ray source spots that are provided in a plane generally perpendicular to a direction of the object's movement, wherein the plurality of ray source spots at least partially surround the object, and emit X-rays toward the object, a first column of detectors comprising a plurality of detection units having a first energy response, wherein the plurality of detection units are provided in a first plane generally parallel to a plane of the first distributed ray source, and configured to receive X-rays penetrating the object, and a second column of detectors comprising a plurality of detection units having a second energy response, wherein the plurality of detection units are provided in a second plane generally parallel to the plane of the first distributed ray source and configured to receive X-rays penetrating the object; a second scanning stage provided in series with the first scanning stage in the direction of the object's movement, comprising: a second distributed ray source comprising a plurality of ray source spots that are provided in a plane generally perpendicular to a direction of the object's movement, wherein the plurality of ray source spots at least partially surround the object, and emit X-rays toward the object, a third column of detectors comprising a plurality of detection units having the first energy response, wherein the plurality of detection units are provided in a third plane generally parallel to the plane of the second distributed ray source and configured to receive X-rays penetrating the object, a fourth column of detectors comprising a plurality of detection units having the second energy response, wherein the plurality of detection units are provided in a fourth plane generally parallel to the plane of the second distributed ray source and configured to receive X-rays penetrating the object; an acquisition device coupled to the first, second, third and fourth columns of detectors, and configured to convert the X-rays detected by the first column of detectors into a first digital signal, the X-rays detected by the second column of detectors into a second digital signal, the X-rays detected by the third column of detectors into a third digital signal, and the X-rays detected by the fourth column of detectors into a fourth digital signal; and a processing device coupled to the acquisition device and configured to reconstruct a CT image of the object based on the first, second, third and fourth digital signals.

In some embodiments, the first distributed ray source generates rays having a spectrum different from that of rays generated by the second distributed ray source.

In some embodiments, the first scanning stage further comprises a fifth column of detectors adjacent to the second column of detectors in the direction of the object's movement, wherein the fifth column of detectors comprise a plurality of detection units having a third energy response, provided in the third plane generally parallel to the plane of the distributed ray source and configured to receive X-rays penetrating the object; the second scanning stage further comprises a sixth column of detectors adjacent to the fourth column of detectors in the direction of the object's movement, wherein the sixth column of detectors comprise a plurality of detection units having the third energy response, provided in the fourth plane generally parallel to the plane of the distributed ray source and configured to receive X-rays penetrating the object; the acquisition device converts the X-rays detected by the fifth and sixth columns of detectors into fifth and sixth digital signals; and the processing device reconstructs a CT image of the object based on the first to sixth digital signals.

According to the above multi-spectral static CT apparatuses, it is possible to solve one or more problems when applying multi-spectral analysis to static CT technology, and to rapidly acquire accurate and complete multi-spectral projection data, for example, without slip-ring rotation. Further, the CT apparatuses can reconstruct images of atomic number and/or electron density of the inspected material, and thus provide improved image quality, more powerful identification of articles, and/or lower cost.

BRIEF DESCRIPTION OF THE DRAWINGS

For a better understanding of the present disclosure, embodiments of the disclosure will be described with reference to the figures, in which:

FIG. 1 illustrates a schematic diagram of a slip ring structure in a conventional CT apparatus;

FIG. 2 illustrates a schematic diagram of a slip ring structure in a conventional dual-energy CT apparatus;

The figures do not illustrate every structure in the embodiments. Throughout the figures, identical reference signs refer to identical or similar components or features.

DETAILED DESCRIPTION OF THE EMBODIMENTS

The particular embodiments of the disclosure are described below in details. It shall be noted that the embodiments herein are used for illustration only, and are not limiting of the disclosure. In the description below, a number of particular details are explained to provide a better understanding of the disclosure. However, it is apparent to those skilled in the art that the disclosure can be implemented without these particular details. In other examples, well-known circuits, materials or methods are not described so as not to obscure the disclosure.

Throughout the specification, reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurring at various positions throughout the specification may not refer to one and the same embodiment or example. Furthermore, specific features, structures or properties may be combined into one or several embodiments or examples in any appropriate way. Moreover, it should be understood by those skilled in the art that the figures here are for the purpose of illustration, and not necessarily drawn to scale. It should be appreciated that "connecting" or "coupling" a component to another component may mean that the component is directly connected or coupled to the other component, or there may be a component intervening between them. On the contrary, "directly connecting" or "directly coupling" a component to another component means that there is no intervening component. Like reference signs refer to similar elements throughout the figures. The term "and/or" used herein means any and all combinations of one or more listed items.

Figure 3:
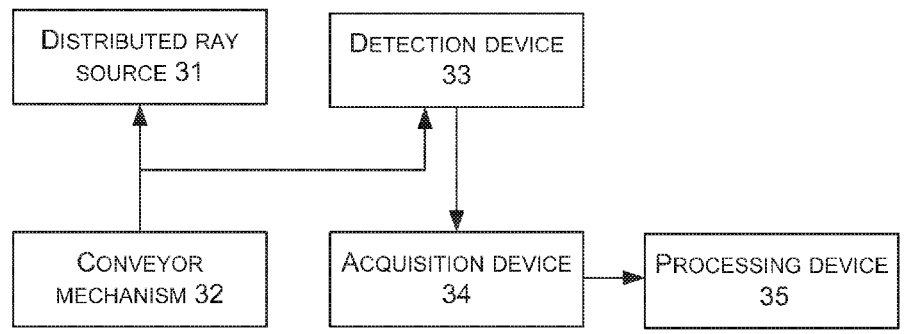
FIG. 3 illustrates a block diagram of a CT apparatus according to an embodiment of the disclosure.

In view of the problems with conventional multi-spectral static CT apparatuses and to rapidly acquire accurate and complete multi-spectral projection data, for example, without slip-ring rotation, some embodiments of the present disclosure propose a multi-spectral static CT apparatus as shown in FIG. 3. The apparatus includes a conveyor mechanism 32, a distributed ray source 31, a detection device 33, an acquisition device 34, and a processing device 35.

The conveyor mechanism 32 carries and moves linearly an object under inspection.

The distributed ray source 31 includes a plurality of ray source spots that are provided in a plane generally perpendicular to a direction of the object's movement. The plurality of ray source spots at least partially surround the object, and emit X-rays toward the object. Each of the ray source spots may be, for example, a carbon-nanotube X-ray tube. In some embodiments, the distributed ray source 31 comprises a plurality of distributed X-ray sources. Energy for ray beam emission can be set for each of the X-ray sources, and a sequence for ray beam emission can be set for all the X-ray sources. The X-ray sources may be arranged in one or more planes, and the X-ray sources in each plane is classified into a group. X-ray sources in the same group may be set to have the same energy for beam emission, while X-ray sources in different groups may be set to have different energy levels for beam emission. The X-ray sources may be arranged in a continuous line or arc, or in multiple segments of discontinuous line or arc. However, X-ray sources in the same group have the same arrangement, so that no deviation of projection data occurs between data of multiple spectra.

In an embodiment, the detection device 33 includes a first column of detectors and a second column of detectors adjacent to the first column of detectors in the direction of the object's movement. The first column of detectors includes a plurality of detection units having a first energy response, the detection units provided in a first plane generally parallel to a plane of the distributed ray source and configured to receive X-rays penetrating the object. The second column of detectors includes a plurality of detection units having a second energy response, the detection units provided in a second plane generally parallel to the plane of the distributed ray source and configured to receive X-rays penetrating the object.

In some embodiments, the plane in which each X-ray source is arranged corresponds to a set of detectors arranged in columns. The detection units in each column of detectors may be arranged in a continuous line or arc, or in multiple segments of discontinuous line or arc. In an embodiment, the respective columns are arranged substantially parallel to each other in the direction of the object's movement, thereby avoiding the problem of oblique incidence of rays due to the arrangement of front and rear columns along the rays. The detection units in each column of detectors may have different energy responses to X-rays emitted from the corresponding group of X-ray sources (X-rays have an energy range that is a set value between 0 and the energy for beam emission) by using different materials or materials of different thicknesses for detection, or placing different filters in front of the detectors. For example, at least one of the first and second columns of detectors has filters. The first energy response is a response substantially to a low energy component in the X-rays, and the second energy response is a response substantially to a high energy component in the X-rays. The processing device reconstructs high-energy and low-energy attenuation coefficient images of the object based on the first and second digital signals. Since different groups of X-ray sources are set to have different energy levels for beam emission, the multiple columns of detectors corresponding to two or more groups of X-ray sources can detect a larger energy range and more energy spectra, and thus obtain a more accurate, finer result of multi-spectral analysis.

The acquisition device 34 is coupled to the detection device 33, and configured to convert the X-rays detected by the first column of detectors into a first digital signal and the X-rays detected by the second column of detectors into a second digital signal. The acquisition device 34 may perform high-speed sampling on electric signals outputted from all the detection units, and convert the electric signals into digital signals to be provided to the processing device 35.

The processing device 35 is coupled to the acquisition device 34 and configured to reconstruct a CT image of the object based on the first and second digital signals. For example, the processing device 35 may reconstruct values of atomic number and/or electron density of the object based on the first and second digital signals.

In some embodiments, a luggage carrying and control device carries the object and moves it past an imaging region surrounded by the distributed ray source, the detection device and the acquisition device. The luggage carrying and control device controls each X-ray source to emit ray beams at the set energy and sequence, and controls the multiple columns of detectors and the acquisition device to perform high-speed sampling at a set time interval or according to an external trigger signal.

Systems that use two or more groups of X-ray sources require an additional process of data registration among a plurality of imaging planes. The luggage carrying and control device may provide, for each group of samples, location index or time index of the object. The data processing device may extract registered multi-spectral projection data in connection with distances between the imaging planes or time differences during the object's passage through the imaging planes.

The processing device 35 is configured to reconstruct from the multi-spectral projection data 3D images of the atomic number and/or electron density of the object.

In an example of dual-energy projection data, the high and low energy projection data obtained from the dual-energy detector are denoted as $p_1$ and $p_2$. The data first undergo pre-processing and correction, such as background and gain correction, or flawed detector track correction. Then, a base material decomposition method is used to dual-energy decompose fan-beam projection data obtained by rearranging the projection data, and obtain dual-energy decomposition coefficients $A_1$ and $A_2$ under different base materials. A CT reconstruction algorithm is used to reconstruct on the two coefficients, and a result of the reconstruction, $\alpha_1$ and $\alpha_2$, is obtained.

Next, distribution values of atomic number $Z$ and/or electron density $\rho_e$ are solved with the following respective formula:

$$Z = \left[ \frac{a_1 \rho_{e1} Z_1^{3.5} + a_2 \rho_{e2} Z_2^{3.5}}{a_1 \rho_{e1} + a_2 \rho_{e2}} \right]^{1/3.5} \quad (1)$$

$$\rho_e = a_1 \rho_{e1} + a_2 \rho_{e2} \quad (2)$$

In the formula, $Z_1$ and $Z_2$ denote values of atomic numbers of two base materials, and $\rho_{e1}$ and $\rho_{e2}$ denote values of electron densities of the two base materials. The above dual-energy reconstruction method first decomposes the projection data and then performs reconstruction, and thus this method is called a pre-processing algorithm. A post-processing method may also be used to first perform CT reconstruction on high and low energy projection data, respectively, and then calculate an image of distribution of materials based on the reconstructed high and low energy attenuation coefficient images. The post-processing method has an advantage of simple and rapid calculation, and a high accuracy even when materials of the scanned object are similar.

Figure 4A:
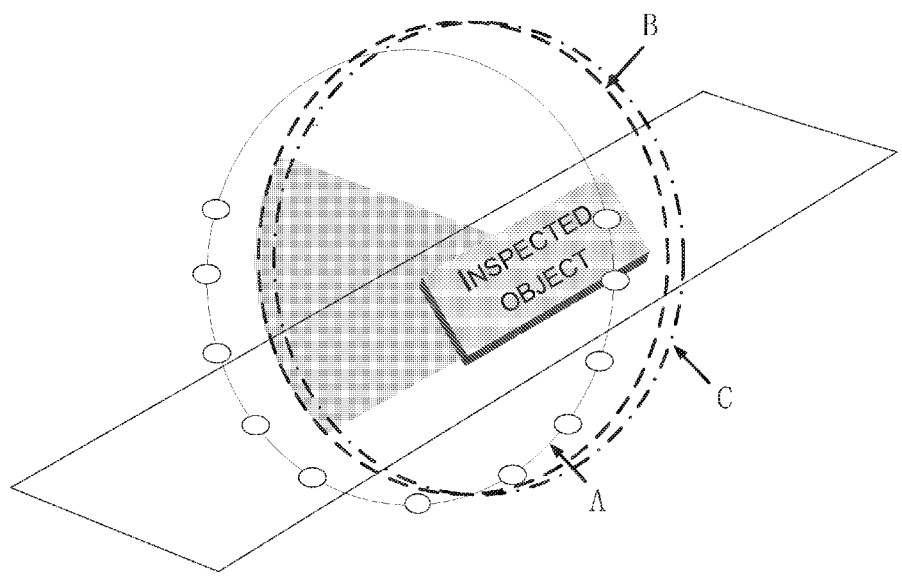
FIG. 4A illustrates a schematic block diagram of a CT apparatus according to an embodiment of the disclosure.
Figure 4B:
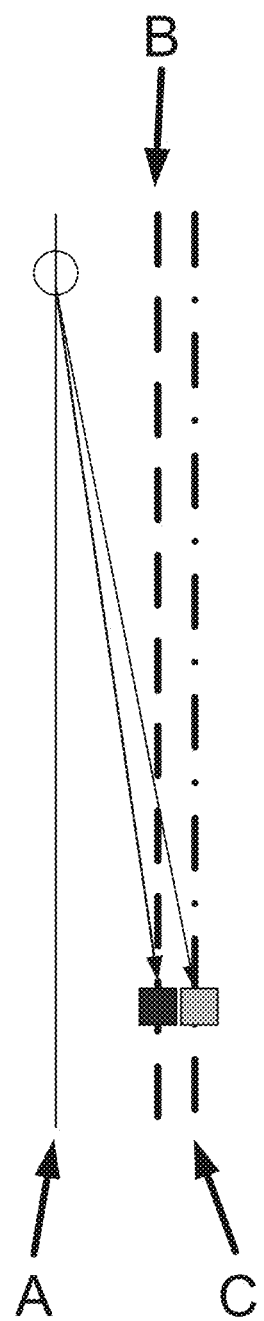
FIG. 4B illustrates a side view of a scanning stage in the CT apparatus of FIG. 4A.

FIG. 4A illustrates a schematic block diagram of a CT apparatus according to an embodiment of the disclosure, and FIG. 4B illustrates a side view of a scanning stage in the CT apparatus of FIG. 4A.

As shown in FIGS. 4A and 4B, the multi-spectral static CT apparatus in the embodiment includes a group of distributed X-ray sources A. All the X-ray sources in the group A are set to have the same energy for beam emission. Two columns of detectors corresponding to the distributed X-ray sources A are distributed in parallel in two adjacent planes, and include high energy detectors B and low energy detectors C.

Figure 5:
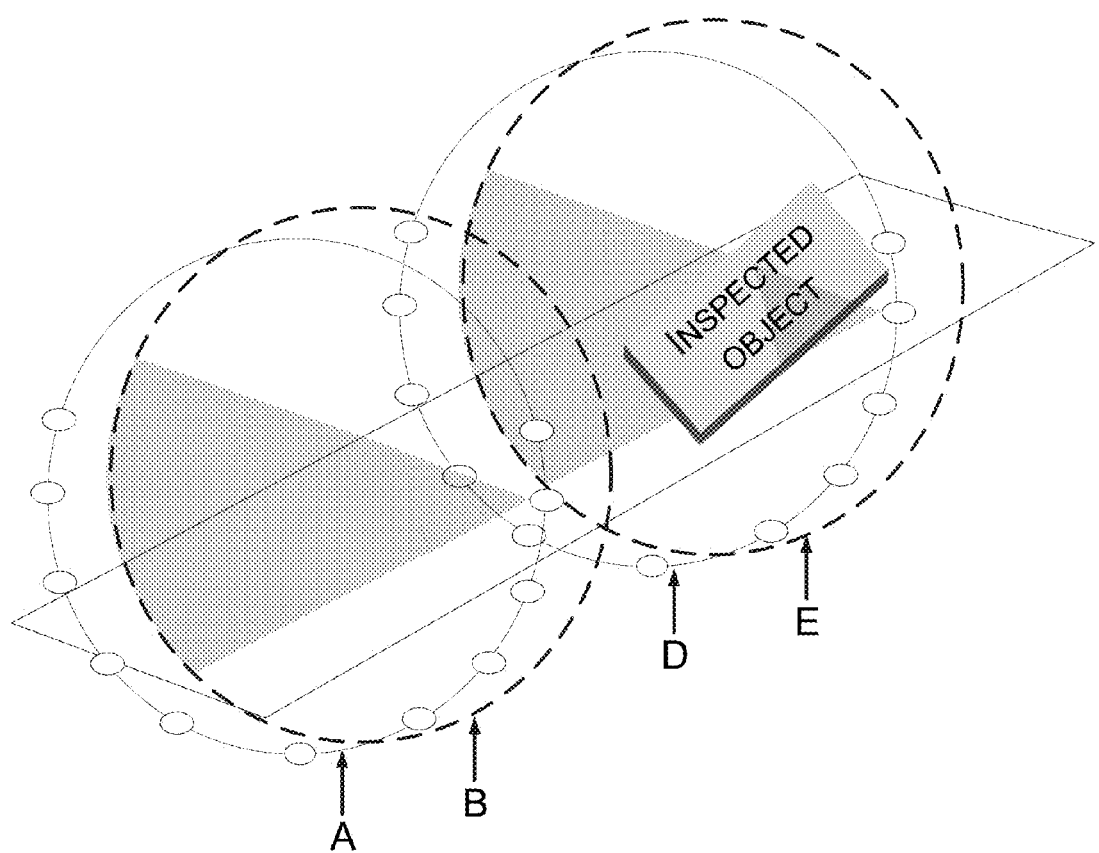
FIG. 5 illustrates a schematic block diagram of a CT apparatus according to another embodiment of the disclosure.

FIG. 5 illustrates a schematic block diagram of a CT apparatus according to another embodiment of the disclosure. As shown in FIG. 5, the multi-spectral static CT apparatus in the embodiment includes at least two scanning stages. The first and second scanning stages use distributed X-ray sources A and D, respectively. The distributed X-ray sources A and D have the same arrangements of X-ray sources. All the X-ray sources in the distributed X-ray source A are set to have the same energy for beam emission, and all the X-ray sources in the distributed X-ray source D are set to have the same energy for beam emission, which is different from the energy for beam emission of the distributed X-ray source A. Two columns of detectors B and E are distributed in generally parallel in two planes, and correspond to the distributed X-ray sources A and D, respectively.

In the embodiment, the conveyor mechanism 32 carries and moves linearly an object under inspection. The first scanning stage includes a first distributed ray source, a first column of detectors and a second column of detectors.

The first distributed ray source includes a plurality of ray source spots that are provided in a plane generally perpendicular to a direction of the object's movement. The plurality of ray source spots at least partially surround the object, and emit X-rays toward the object. The first column of detectors includes a plurality of detection units having a first energy response. The plurality of detection units are provided in a first plane generally parallel to a plane of the first distributed ray source, and configured to receive X-rays penetrating the object.

The second scanning stage is provided in series with the first scanning stage in the direction of the object's movement, and includes a second distributed ray source and a second column of detectors. The second distributed ray source includes a plurality of ray source spots that are provided in a plane generally perpendicular to a direction of the object's movement. The plurality of ray source spots at least partially surround the object, and emit X-rays toward the object. The second column of detectors includes a plurality of detection units having a second energy response. The plurality of detection units are provided in a second plane generally parallel to the plane of the second distributed ray source and configured to receive X-rays penetrating the object.

In the embodiment, the acquisition device 34 is coupled to the first and second columns of detectors, and configured to convert the X-rays detected by the first column of detectors into a first digital signal and the X-rays detected by the second column of detectors into a second digital signal. The processing device 35 is coupled to the acquisition device and configured to reconstruct a CT image of the object based on the first and second digital signals.

Figure 6:
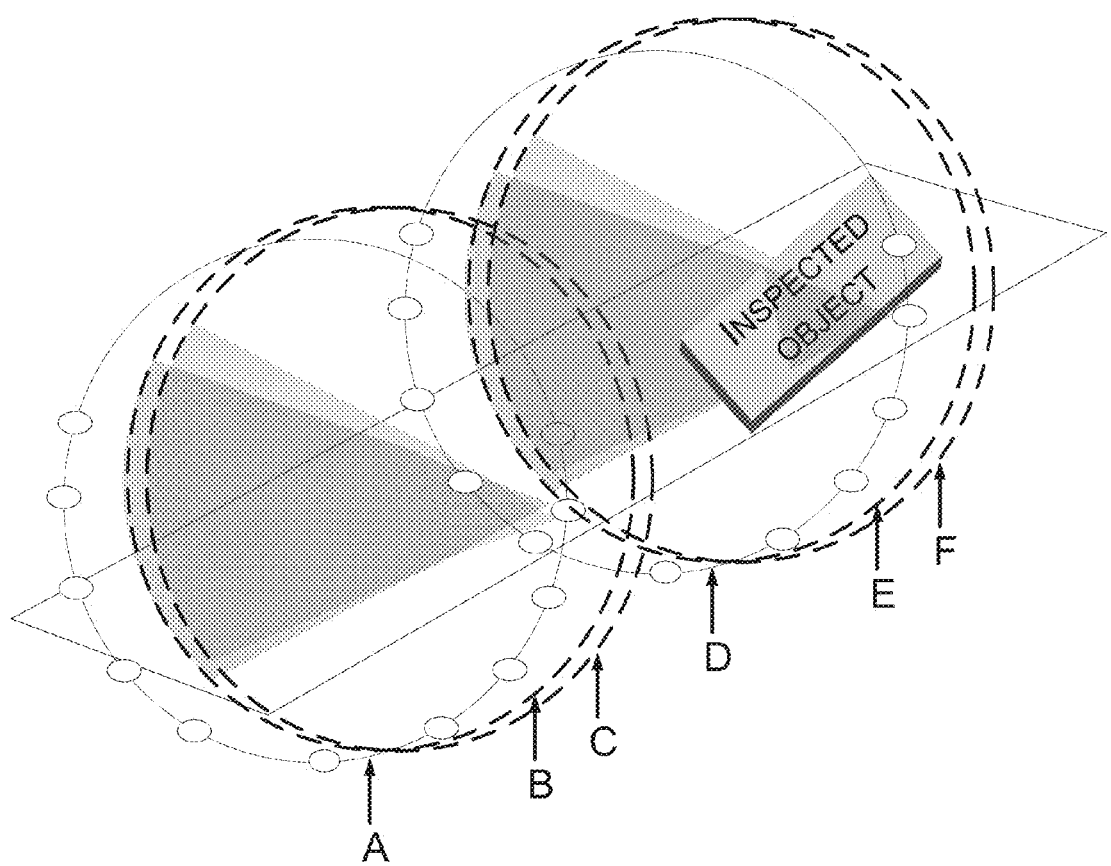
FIG. 6 illustrates a schematic block diagram of a CT apparatus according to a further embodiment of the disclosure.

FIG. 6 illustrates a schematic block diagram of a CT apparatus according to a further embodiment of the disclosure. As shown in FIG. 6, the multi-spectral static CT apparatus in the embodiment includes at least two scanning stages. The first and second scanning stages use distributed X-ray sources A and D, respectively. All the X-ray sources in the distributed X-ray source A are set to have the same energy for beam emission, and all the X-ray sources in the distributed X-ray source D are set to have the same energy for beam emission, which is maintained as different from the energy for beam emission of the distributed X-ray source A. The distributed X-ray sources A and D have the same arrangements of X-ray sources. Four columns of detectors B, C, E, and F are distributed generally in parallel in four planes. The two columns of detectors B and C corresponding to the distributed X-ray source A are adjacent to each other, have different energy responses, and used to detect X-rays emitted by the distributed X-ray source A. The two columns of detectors E and F corresponding to the distributed X-ray source D are adjacent to each other, have different energy responses, and used to detect X-rays emitted by the distributed X-ray source D.

In the embodiment, the conveyor mechanism 32 carries and moves linearly an object under inspection. The first scanning stage includes a first distributed ray source, a first column of detectors and a second column of detectors.

The first distributed ray source includes a plurality of ray source spots that are provided in a plane generally perpendicular to a direction of the object's movement. The plurality of ray source spots at least partially surround the object, and emit X-rays toward the object. The first column of detectors includes a plurality of detection units having a first energy response. The plurality of detection units are provided in a first plane generally parallel to a plane of the first distributed ray source, and configured to receive X-rays penetrating the object. The second column of detectors includes a plurality of detection units having a second energy response. The plurality of detection units are provided in a second plane generally parallel to the plane of the first distributed ray source and configured to receive X-rays penetrating the object.

The second scanning stage is provided in series with the first scanning stage in the direction of the object's movement, and includes a second distributed ray source, a third column of detectors, and a fourth column of detectors.

The second distributed ray source includes a plurality of ray source spots that are provided in a plane generally perpendicular to a direction of the object's movement. The plurality of ray source spots at least partially surround the object, and emit X-rays toward the object. The third column of detectors includes a plurality of detection units having the first energy response. The plurality of detection units are provided in a third plane generally parallel to the plane of the second distributed ray source and configured to receive X-rays penetrating the object. The fourth column of detectors includes a plurality of detection units having the second energy response. The plurality of detection units are provided in a fourth plane generally parallel to the plane of the second distributed ray source and configured to receive X-rays penetrating the object.

The acquisition device 34 is coupled to the first, second, third and fourth columns of detectors, and configured to convert the X-rays detected by the first column of detectors into a first digital signal, the X-rays detected by the second column of detectors into a second digital signal, the X-rays detected by the third column of detectors into a third digital signal, and the X-rays detected by the fourth column of detectors into a fourth digital signal.

The processing device 35 is coupled to the acquisition device and configured to reconstruct a CT image of the object based on the first, second, third and fourth digital signals.

In the above embodiments, each scanning stage in the CT apparatus includes two columns of detectors. Those skilled in the art would appreciate that a larger number of detector arrays may be used. For example, a generally parallel-arranged third column of detectors may be included in the first scanning stage, and a fourth column of detectors may be included in the second scanning stage. Further, in some embodiments, the ray spectra of the first and second distributed ray sources may be set to be identical to or different from each other as required, or may be set to be partially overlapped.

The multi-spectral static CT imaging systems in the described embodiments use distributed ray sources to irradiate luggage or articles from different angles, without the slip-ring rotation in the conventional CT systems. This provides high security and reliability, reduces system cost and improves scanning speed. Meanwhile, by incorporating the multi-spectral analysis technology, the CT imaging systems can obtain atomic number and/or electron density at any location inside the luggage or article. This provides more intuitive information for further applications, such as detection of dangerous substances or smuggled products. The CT imaging systems can be applied widely for rapid and accurate detection of contraband articles, like explosives, inflammable substances or drugs.

The embodiments of the present disclosure are characterized not only in combination of the static CT technology and the multi-spectral analysis technology, but also in skillful design and arrangement of the distributed ray source and multiple columns of detectors in the system. With the embodiments of the present disclosure, it is possible to avoid the problems of oblique incidence of rays and projection data deviation between multi-spectral data that occurs in a CT system with a slip ring during a multi-spectral analysis process. In this way, accuracy in resolution of CT reconstructed images and spectral analysis results can be guaranteed.

The foregoing detailed description has set forth various embodiments via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following; a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not as a limitation. The present disclosure may be practiced in various forms without departing from the spirit or essence of the disclosure. It should be understood that the embodiments are not limited to any of the foregoing details, and shall be interpreted broadly within the spirit and scope as defined by the following claims. Therefore, modifications and alternatives falling within the scope of the claims and equivalents thereof are to be encompassed by the scope of the present disclosure which is defined by the claims as attached.

What is claimed is:

1. A multi-spectral static Computerized Tomography (CT) apparatus, comprising:
   a conveyor mechanism configured to carry and move an object under inspection in a direction along a path;
   a distributed ray source comprising a plurality of ray source spots that are provided in a plane generally perpendicular to the direction of the object's movement, wherein the plurality of ray source spots at least partially surround the path of the object, and are configured to emit X-rays toward the path in order to penetrate the object;
   a detection device comprising a plurality of detection units configured to receive X-rays penetrating the object and having a first energy response, the plurality of detection units having the first energy response provided in a first plane generally parallel to a plane of the distributed ray source such that at least one detection unit of the detection units having the first energy response is at an opposite side of the path passing through the first plane to at least one other detection unit of the detection units having the first energy response, and comprising a plurality of detection units configured to receive X-rays penetrating the object and having a second energy response, the plurality of detection units having the second energy response provided adjacent to the plurality of detection units having the first energy response in the direction of the object's movement and the plurality of detection units having the second energy response provided in a second plane generally parallel to the plane of the distributed ray source such that at least one detection unit of the detection units having the second energy response is at an opposite side of the path passing through the second plane to at least one other detection unit of the detection units having the second energy response;
   an acquisition device coupled to the detection device and configured to convert the X-rays detected by the detection units having the first energy response into a first digital signal and the X-rays detected by the detection units having the second energy response into a second digital signal; and
   a processing device coupled to the acquisition device and configured to reconstruct a CT image of the object based on the first and second digital signals.

2. The CT apparatus according to claim 1, wherein the detection units having the first energy response and/or detection units having the second energy response have filters.

3. The CT apparatus according to claim 2, wherein each of the ray source spots comprises a carbon-nanotube X-ray tube.

4. The CT apparatus according to claim 1, wherein the first energy response is a response substantially to a low energy component in the X-rays, and the second energy response is a response substantially to a high energy component in the X-rays; and
   the processing device is configured to reconstruct high-energy and low-energy attenuation coefficient images of the object based on the first and second digital signals.

5. The CT apparatus according to claim 4, wherein the processing device is configured to reconstruct values of atomic number and/or electron density of the object based on the first and second digital signals.

6. The CT apparatus according to claim 1, wherein the detection device further comprises a plurality of detection units configured to receive X-rays penetrating the object and having a third energy response, the plurality of detection units having the third energy response provided adjacent to the plurality of detection units having the second energy response in the direction of the object's movement and the plurality of detection units having the third energy response provided in a third plane generally parallel to the plane of the distributed ray source;
   the acquisition device converts the X-rays detected by the detection units having the third energy response of detectors into a third digital signal; and
   the processing device is configured to reconstruct a CT image of the object based on the first, second and third digital signals.

7. A multi-spectral static Computerized Tomography (CT) apparatus, comprising:
   a conveyor mechanism configured to carry and move an object under inspection in a direction along a path;
   a first scanning stage comprising:
      a first distributed ray source comprising a plurality of ray source spots that are provided in a plane generally perpendicular to a direction of the object's movement, wherein the plurality of ray source spots at least partially surround the path of the object, and are configured to emit X-rays toward the path in order to penetrate the object, and a plurality of detection units configured to receive X-rays penetrating the object and having a first energy response, wherein the plurality of detection units having the first energy response are provided in a first plane generally parallel to a plane of the first distributed ray source such that at least one detection unit of the detection units having the first energy response is at an opposite side of the path passing through the first plane to at least one other detection unit of the detection units having the first energy response;

a second scanning stage provided in series with the first scanning stage in the direction of the object's movement, the second scanning stage comprising:

a second distributed ray source comprising a plurality of ray source spots that are provided in a plane generally perpendicular to a direction of the object's movement, wherein the plurality of ray source spots at least partially surround the path of the object, and are configured to emit X-rays toward the path in order to penetrate the object, and a plurality of detection units configured to receive X-rays penetrating the object and having a second energy response, wherein the plurality of detection units having the second energy response are provided in a second plane generally parallel to the plane of the second distributed ray source such that at least one detection unit of the detection units having the second energy response is at an opposite side of the path passing through the second plane to at least one other detection unit of the detection units having the second energy response;

an acquisition device configured to convert the X-rays detected by the detection units having the first energy response into a first digital signal and the X-rays detected by the detection units having the second energy response into a second digital signal; and a processing device coupled to the acquisition device and configured to reconstruct a CT image of the object based on the first and second digital signals.

8. The CT apparatus according to claim 7, wherein the first distributed ray source generates rays having a spectrum different from that of rays generated by the second distributed ray source.

9. The CT apparatus according to claim 7, wherein the plurality of detection units having the first energy response and/or plurality of detection units having the second energy response have filters.

10. The CT apparatus according to claim 7, wherein each of the ray source spots comprises a carbon-nanotube X-ray tube.

11. The CT apparatus according to claim 7, wherein the first energy response is a response substantially to a low energy component in the X-rays, and the second energy response is a response substantially to a high energy component in the X-rays; and the processing device is configured to reconstruct high-energy and low-energy attenuation coefficient images of the object based on the first and second digital signals.

12. The CT apparatus according to claim 11, wherein the processing device is configured to reconstruct values of atomic number and/or electron density of the object based on the first and second digital signals.

13. A multi-spectral static Computerized Tomography (CT) apparatus, comprising:

a conveyor mechanism configured to carry and move an object under inspection in a direction along a path;

a first scanning stage comprising:

a first distributed ray source comprising a plurality of ray source spots that are provided in a plane generally perpendicular to a direction of the object's movement, wherein the plurality of ray source spots at least partially surround the path of the object, and are configured to emit X-rays toward the path in order to penetrate the object, a first plurality of detection units configured to receive X-rays penetrating the object and having a first energy response, wherein the first plurality of detection units having the first energy response are provided in a first plane generally parallel to a plane of the first distributed ray source such that at least one detection unit of the first plurality of detection units having the first energy response is at an opposite side of the path passing through the first plane to at least one other detection unit of the first plurality of detection units having the first energy response, and a first plurality of detection units configured to receive X-rays penetrating the object and having a second energy response, wherein the first plurality of detection units having the second energy response are provided in a second plane generally parallel to the plane of the first distributed ray source such that at least one detection unit of the first plurality of detection units having the second energy response is at an opposite side of the path passing through the second plane to at least one other detection unit of the first plurality of detection units having the second energy response;

a second scanning stage provided in series with the first scanning stage in the direction of the object's movement, the second scanning stage comprising:

a second distributed ray source comprising a plurality of ray source spots that are provided in a plane generally perpendicular to a direction of the object's movement, wherein the plurality of ray source spots at least partially surround the path of the object, and are configured to emit X-rays toward the path in order to penetrate the object, a second plurality of detection units configured to receive X-rays penetrating the object and having the first energy response, wherein the second plurality of detection units having the first energy response are provided in a third plane generally parallel to the plane of the second distributed ray source such that at least one detection unit of the second plurality of detection units having the first energy response is at an opposite side of the path passing through the third plane to at least one other detection unit of the second plurality of detection units having the first energy response, a second plurality of detection units configured to receive X-rays penetrating the object and having the second energy response, wherein the second plurality of detection units having the second energy response are provided in a fourth plane generally parallel to the plane of the second distributed ray source such that at least one detection unit of the second plurality of detection units having the second energy response is at an opposite side of the path passing through the fourth plane to at least one other detection unit of the second plurality of detection units having the second energy response;

an acquisition device configured to convert the X-rays detected by the first plurality of detection units having the first energy response into a first digital signal, the X-rays detected by the first plurality of detection units having the second energy response into a second digital signal, the X-rays detected by the second plurality of detection units having the first energy response into a third digital signal, and the X-rays detected by the second plurality of detection units having the second energy response into a fourth digital signal; and a processing device coupled to the acquisition device and configured to reconstruct a CT image of the object based on the first, second, third and fourth digital signals.

14. The CT apparatus according to claim 13, wherein the first distributed ray source generates rays having a spectrum different from that of rays generated by the second distributed ray source.

15. The CT apparatus according to claim 13, wherein
the first scanning stage further comprises a first plurality of detection units configured to receive X-rays penetrating the object and having a third energy response, the first plurality of detection units having the third energy response provided adjacent to the first plurality of detection units having the second energy response in the direction of the object's movement and the first plurality of detection units having the third energy response provided in a plane generally parallel to the plane of the first distributed ray source;

the second scanning stage further comprises a second plurality of detection units configured to receive X-rays penetrating the object and having the third energy response, the second plurality of detection units having the third energy response provided adjacent to the second plurality of detection units having the second enemy response in the direction of the object's movement and the second plurality of detection units having the third energy response provided in a plane generally parallel to the plane of the second distributed ray source;

the acquisition device converts the X-rays detected by the first plurality of detection units having the third energy response and the second plurality of detection units having the third energy response into fifth and sixth digital signals respectively; and the processing device is configured to reconstruct a CT image of the object based on the first to sixth digital signals.

16. The CT apparatus according to claim 13, wherein the first plurality of detection units having the first energy response and/or first plurality of detection units having the second energy response have filters.

17. The CT apparatus according to claim 13, wherein each of the ray source spots comprises a carbon-nanotube X-ray tube.

18. The CT apparatus according to claim 13, wherein the first energy response is a response substantially to a low energy component in the X-rays, and the second energy response is a response substantially to a high energy component in the X-rays; and the processing device is configured to reconstruct high-energy and low-energy attenuation coefficient images of the object based on the first, second, third and fourth digital signals.

19. The CT apparatus according to claim 18, wherein the processing device is configured to reconstruct values of atomic number and/or electron density of the object based on the first, second, third and fourth digital signals.

* * * * *